US008572781B2

(12) United States Patent
Schlanger et al.

(10) Patent No.: US 8,572,781 B2
(45) Date of Patent: Nov. 5, 2013

(54) PORTABLE EXTREMITY ASSESSMENT AND MANAGEMENT DEVICE (75) Inventors: Richard E. Schlanger, Dublin, OH (US); Patsy E. Martinsek, Columbus, OH (US)

(73) Assignee: The Ohio State University, Columbus, OH (US)

(*) Notice: Subject to any disclaimer, the term of this patent is extended or adjusted under 35 U.S.C. 154(b) by 378 days.

(21) Appl. No.: 12/920,254

(22) PCT Filed: Mar. 2, 2009

(86) PCT No.: PCT/US2009/035740
§ 371 (c)(1), (2), (4) Date: Aug. 30, 2010

(87) PCT Pub. No.: WO2009/108938
PCT Pub. Date: Sep. 3, 2009

(65) Prior Publication Data
US 2011/0000022 A1    Jan. 6, 2011

Related U.S. Application Data (60) Provisional application No. 61/032,596, filed on Feb. 29, 2008.

(51) Int. Cl.
A47C 20/00 (2006.01)
A47C 16/00 (2006.01)

(52) U.S. Cl.
USPC .................................................. 5/648; 5/646

(58) Field of Classification Search
USPC .......... 5/646, 648, 623, 624, 634; 602/20, 23, 602/32
See application file for complete search history.

(56) References Cited

U.S. PATENT DOCUMENTS

| 830,776 | A | * | 9/1906 | Flagg | 5/648 |
| 1,296,722 | A | | 3/1919 | Washburn | |
| 2,020,262 | A | | 11/1935 | Longfellow | |
| 2,502,752 | A | | 4/1950 | Richards | |
| 2,581,110 | A | * | 1/1952 | Kenworthy | 297/423.46 |
| 2,722,692 | A | | 11/1955 | Dempster | |
| 3,066,322 | A | * | 12/1962 | Derby | 5/651 |
| 3,430,956 | A | * | 3/1969 | Borgeas | 482/79 |
| 5,000,168 | A | | 3/1991 | Lipson | |
| 5,054,144 | A | * | 10/1991 | Stuart et al. | 5/648 |
| 5,111,808 | A | | 5/1992 | Meals | |

(Continued)

OTHER PUBLICATIONS

LIFT-A-LIMB Lower Extremity, Nov. 17, 2006, pp. 1-2, www.liftalimb.com/product/LAL29-11.

*Primary Examiner* — Robert G Santos
(74) *Attorney, Agent, or Firm* — Jason H. Foster; Kremblas & Foster (57) ABSTRACT

A device and method for elevating and supporting a patient's extremity to facilitate convenient examination and treatment of the extremity. The device includes a base, longitudinally-spaced upstanding support members extending upwardly from the base, and extremity securing mechanisms mounted to the upstanding support members upon which a patient's extremity can be positioned. The method generally includes extending a patient's extremity longitudinally across the extremity securing mechanisms and bringing the extremity to rest thereon. Caregivers and surgical teams are thus provided with access to the full circumference of the portion of the patient's extremity that extends between the extremity securing mechanisms. Several embodiments of the device incorporate means for assisting in the lifting of a patient's extremity to a desired height, including hydraulic rams, levers, and inflatable bladders.

6 Claims, 7 Drawing Sheets

(56) References Cited

U.S. PATENT DOCUMENTS

| | | |
|---|---|---|
| 5,418,991 A | 5/1995 | Shiflett |
| 6,012,456 A | 1/2000 | Schuerch |
| 6,026,812 A | 2/2000 | Lipson et al. |
| 6,764,458 B2 * | 7/2004 | Polonchek ............... 602/32 |
| 6,874,184 B2 | 4/2005 | Chandler |
| 6,986,181 B2 * | 1/2006 | Murphy et al. ............... 5/648 |
| 7,156,820 B2 * | 1/2007 | Polonchek ............... 602/32 |
| 8,336,142 B1 * | 12/2012 | See et al. ............... 5/634 |
| 2002/0023298 A1 | 2/2002 | Lamb et al. |
| 2003/0078144 A1 | 4/2003 | Gehrke |
| 2003/0154550 A1 * | 8/2003 | Murphy et al. ............... 5/648 |
| 2004/0059268 A1 * | 3/2004 | Polonchek ............... 601/33 |
| 2004/0204668 A1 * | 10/2004 | Polonchek ............... 602/32 |
| 2005/0080371 A1 | 4/2005 | March et al. |
| 2007/0163048 A1 | 7/2007 | Kimball |
| 2011/0000022 A1 * | 1/2011 | Schlanger et al. ............... 5/630 |
| 2012/0324650 A1 * | 12/2012 | Russell ............... 5/648 |

* cited by examiner

PORTABLE EXTREMITY ASSESSMENT AND MANAGEMENT DEVICE

BACKGROUND OF THE INVENTION

1. Field of the Invention

The present invention relates generally to methods and devices for inspecting and treating affected surfaces of a patient's extremities, such as limbs, and relates more particularly to methods and devices for elevating and supporting a patient's affected extremity to allow full assessment of, and access to the extremity to facilitate proper care and treatment, including performing surgical procedures.

2. Description of the Related Art

Patients who suffer from acute or chronic wounds, edema, and other conditions that affect the skin and that penetrate dermal layers, or who are subject to amputation, debridement, or other surgical applications, often require skilled care or hospitalization for proper assessment and treatment. "Acute" wounds are defined as wounds that are generally less than 30 days old, such as those resulting from trauma, burns, or surgery. "Chronic" wounds are defined as wounds that are generally greater than 30 days old, such as diabetic ulcers, venous stasis ulcers, arterial ulcers, non-healing surgical wounds, cancerous lesions, or pressure ulcers. "Edema" is defined as the abnormal accumulation of fluid beneath the skin, often resulting from renal failure, congestive heart failure, and other cardiovascular diseases.

During the assessment and treatment of conditions such as those described above, two or more caregivers are commonly required to manually elevate and stabilize a patient's extremity in order to conduct a proper visual inspection of an affected area (i.e., areas affected by any of the conditions described above) and to administer any required treatments. In some cases, it is necessary to elevate a patient's extremity using manual force for extended periods of time while treatments are administered. Providing care in such a manner can be extremely labor-intensive, time-consuming, and can expose caregivers to the risk of back or other injuries. Moreover, the patient may be caused undue stress during the process of being forcefully moved and manipulated, possibly resulting in further injury. Furthermore, the physical effort required to properly elevate and stabilize the patient's extremity may exceed that which can be provided by the attendant caregivers, especially in the case of larger patients. For example, it may be necessary to stabilize a patient's leg to facilitate a surgical procedure such as amputation. Providing the requisite stability by manually holding the leg may be impossible if the weight of the leg is greater than can be supported by attendant caregivers.

To reduce stress or injury to themselves and to provide greater comfort to patients during examination and treatment, caregivers in a variety of settings will often attempt to elevate and support patients' extremities using pillows or cushions. This method can be effective in some situations, such as where only a small area of a patient's extremity requires treatment. However, pillows, cushions, and similar supportive structures have the disadvantage of blocking access to the lower surfaces of extremities that rest upon them, such as the underside of an arm or a leg. Using such structures for support is therefore ineffective in situations where caregivers or surgeons are required to view or access most or all of the circumference of a patient's affected extremity, such when the extremity must be wrapped in bandaging or during extensive debridement (i.e., the removal of dead, damaged, or infected tissue). Furthermore, such supportive structures still require manual effort to lift an extremity onto them.

Over the past several decades, a number of devices have been developed to assist caregivers with supporting a patient's affected limb during medical examination and treatment. For example, U.S. Pat. Nos. 6,874,184 to Chandler, 6,026,812 to Lipson et. al, and 5,000,168 to Lipson all describe devices that cradle the lower surface of a patient's extremity while providing convenient visualization of, and access to, an upper surface of the extremity. However, as with the pillows and cushions discussed above, each of these devices blocks access to the full circumference of the supported extremity.

In view of the numerous difficulties associated with the assessment and treatment of a patient's affected extremities and the persistent increase in obesity and related indications that make it difficult to manually lift and stabilize such extremities, it would be advantageous to have a method and device for lifting and supporting a patient's extremity while reducing stress on both the patient and attendant caregivers. It would further be advantageous to have such a method and device for providing full access to the affected areas of the extremity to facilitate assessment, visualization, photography, measurement, wound management, treatment, and surgery. It would further be advantageous to have such a method and device that can be reconfigured to accommodate various different sizes of extremities and that can be easily sanitized. It would further be advantageous to have such a device and method that can be adapted for use in a variety of home, moderate care, clinical, hospital, and surgical settings.

BRIEF SUMMARY OF THE INVENTION

In accordance with the present invention, there is provided a device and method for supporting and isolating any of a patient's various extremities, including the arms, hands, legs, feet, and head of a patient during medical assessment and treatment of such extremities. The device is configured to allow full access to substantially all areas of a patient's supported extremity to facilitate anesthesia, recovery from surgery, and convenient treatment and care of wounds, ulcers, and other conditions without placing undue burden on the patient or on attendant caregivers. It is contemplated that the device can be used in hospitals, wound care centers, nursing homes, home health agencies, in home care settings, and in comparable environments for veterinary applications.

According to a first embodiment of the present invention, there is provided a device having a rectangular base, four spaced, upstanding support members extending in a parallel relationship to one another from the four corners of the base, and two extremity securing mechanisms that each extend across a laterally-opposing pair of upstanding support members. The base and the upstanding support members are preferably formed of elongated, tubular members that are removably joined together for allowing the base to be disassembled or extended (described below) for storage and transportation. The device is preferably provided with elongated extension segments that can be axially mounted to the segments of the base or to the upstanding support members with adapter bits for increasing the dimensions of the device.

The extremity securing mechanisms are preferably formed of flexible straps having resilient support pads mounted thereon. The flexible straps are preferably adjustably mounted to the upstanding support members for allowing the tautness of the extremity securing mechanisms to be adjusted. Each support pad is preferably covered by a removable cover sleeve that can be sanitized or replaced between uses of the device.

To use the device, a patient's extremity is extended across and brought to rest on the longitudinally-spaced, elevated extremity securing mechanisms. For example, the upper calf of a patient's leg can be positioned on one of the extremity securing mechanisms and the patient's ankle can be positioned on the other, distally spaced extremity securing mechanism. Caregivers are thus provided with complete access to the full circumference of the portion of the patient's extremity that extends between the extremity securing mechanisms.

According to a second embodiment of the present invention, there is provided a device that is substantially similar to the first embodiment described above except that the upstanding support members are each pivotably mounted to the base. The upstanding support members are preferably interconnected and are able to be collectively pivoted between an upright position and a collapsed position relative to the base to facilitate convenient storage and transportation of the device. A support stand is preferably mounted to at least one of the upstanding support members for removably engaging any of a series of apertures in the base to support the upstanding support members in a number of upright positions in the manner of a bicycle kickstand during use. An elongated lift bar is preferably also mounted to at least one of the upstanding support members for providing a user with a lever for easily pivoting the upstanding support members between the upright and collapsed positions. Alternatively, it is contemplated that other mechanical or electromechanical means (e.g., pneumatic or hydraulic rams, electric motors, etc.) can be incorporated for pivoting the device between positions. The device includes extremity securing mechanisms that are substantially identical to those of the first embodiment of the device described above.

To use the second embodiment of the inventive device, a patient's extremity is extended across and brought to rest on, the longitudinally-spaced, elevated extremity securing mechanisms while the device is in an upright position. Alternatively, the patient's extremity can be positioned on the extremity securing mechanisms when the device is in a collapsed position, and a caregiver can subsequently pivot the device to its upright position using the lift bar, thereby elevating the patient's extremity with relatively little effort.

According to a third embodiment of the present invention, there is provided a device that includes two elongated, I-beam shaped upstanding support members mounted to a planar base plate in a laterally-extending, longitudinally-spaced, parallel configuration. The device further includes extremity securing mechanisms formed of elongated blocks of resilient, shock absorbent material, and preferably foam rubber, that are affixed to the top surfaces of the upstanding support members. The extremity securing mechanisms preferably also include silicone pads that are positioned on the top surfaces of the foam rubber blocks. Each silicone pad is preferably covered by a removable nylon cover sleeve that can be sanitized or replaced between uses of the device. As with the embodiments of the inventive device described above, a patient's extremity can be extended across and brought to rest on the longitudinally-spaced, elevated extremity securing mechanisms to facilitate examination and treatment of the extremity.

According to a fourth embodiment of the present invention, there is provided a device that includes two upstanding support members extending from opposite ends of a rectangular base. The device further includes first and second lift-pistons that axially protrude from the upstanding support members. The lift-pistons are preferably hydraulically or pneumatically operated and terminate in first and second yokes that are rigidly secured to the tops of the lift-pistons. The yokes cradle and support a patient's extremity during assessment and treatment and can be raised and lowered through actuation of the lift-pistons, such as through manipulation of a foot pedal or other control means, for positioning the extremity at a desired height.

According to a fifth embodiment of the present invention, there is provided a device that includes an H-shaped base having two legs connected by a cross member. The base is formed of a lightweight, resilient material, preferably foam. The device further includes elongated extremity securing mechanisms that are preferably formed of foam block and are preferably removably secured to the top surfaces of the legs of the H-shaped base, such as with Velcro, releasable adhesive, contact tape, or similar means. The extremity securing mechanisms can thereby be easily detached from the base to be sanitized or replaced. As with the embodiments of the inventive device described above, a patient's extremity can be lifted onto and extended across the extremity securing mechanisms of the device for examination and treatment.

According to a sixth embodiment of the present invention, there is provided a device that includes an inflatable bladder having a rectangular base and upstanding support members that together define a contiguous, inflatable chamber. The upstanding support members are walls that extend from each edge of the base, and each of the longitudinally-opposing walls has a central notch formed in its top edge for receiving a patient's extended extremity. The extremity can thus be brought to rest within the notches of the inflated bladder to facilitate examination and treatment. Alternatively, the patient's extremity can be positioned on the device while the bladder is deflated, and the bladder can thereafter be inflated to conveniently raise the extremity to a desired height.

According to a seventh embodiment of the present invention, there is provided a device that includes a wheeled base and a rectangular vertical frame having two parallel, longitudinally-spaced suspension bars extending perpendicularly therefrom. The base is configured to fit below a conventional hospital bed with the longitudinally-spaced support arms extending laterally over the bed. Flexible slings with extremity supporting and pressure-relieving portions are hung from each of the suspension bars by hooks. Each sling thus laterally extends below its respective suspension bar in a slackened, U-shaped configuration.

To use the device, the extremity of a patient lying in a bed positioned under the support arms can be extended through and brought to rest on the longitudinally-aligned slings. For example, the upper calf of a patient's leg can be brought to rest on the sling nearest the head of the bed and the patient's ankle can be brought to rest on the sling nearest the foot of the bed.

According to an eighth embodiment of the present invention, there is provided a device that includes two suspension bars and two slings that are substantially identical to the suspension bars and slings of the seventh embodiment of the device described above. Instead of being connected to a portable frame, however, the suspension bars are affixed to, and laterally extend across, the upper cross members of a canopy-style bed with the slings hanging downwardly therefrom in a longitudinally-spaced relationship. The device is otherwise used in a manner identical to the seventh embodiment of the device, with a patient's extremity being extended through and brought to rest on the slings to facilitate examination and treatment.

Several embodiments of the inventive extremity assessment and management device are described and illustrated in detail herein. Each of the embodiments of the invention facilitates the isolation and stabilization of any of a patient's extremities, including any portion of a patient's head, arms, legs, hands, and feet, in an elevated position for allowing convenient medical examination and treatment of the extremity with minimum stress placed on the patient and attendant caregivers. For example, the spaced contacting supports of the invention facilitate full access to the surfaces of a supported limb for surgical or bedside debridement of dead tissue while maintaining steady positioning of the extremity. The inventive device also allows wounds on an affected extremity to be conveniently inspected, photographed, and measured, such as for the application of therapeutic dressings and surgical intervention. Some of the described embodiments of the inventive device additionally assist in lifting and lowering a patient's extremity to a desired height. The inventive device thus provides virtually complete access to affected areas of a patient's extremities for treatment while minimizing the effort required from caregivers as well as the stress imposed on patients.

In addition to being used to accommodate the extremities of human patients (as further described herein), it is contemplated that all of the embodiments of the device described below can similarly be used to facilitate the examination and treatment of the extremities of various different companion animals, including, but not limited to dogs, cats, and horses, as well as various different livestock animals, including, but not limited to cows, pigs, sheep, donkeys, and goats.

In describing the preferred embodiment of the invention which is illustrated in the drawings, specific terminology will be resorted to for the sake of clarity. However, it is not intended that the invention be limited to the specific term so selected and it is to be understood that each specific term includes all technical equivalents which operate in a similar manner to accomplish a similar purpose. For example, the word "connected" or terms similar thereto are often used. They are not limited to direct connection, but include connection through other elements where such connection is recognized as being equivalent by those skilled in the art.

DETAILED DESCRIPTION OF THE INVENTION

Figure 1:
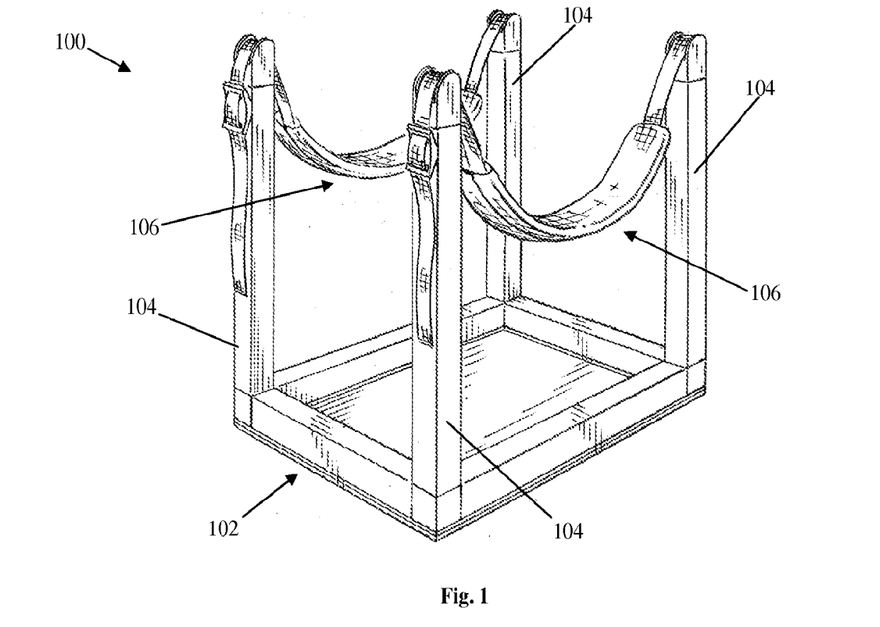
FIG. 1 is a perspective view illustrating a first exemplary embodiment of the present invention.
Figure 2:
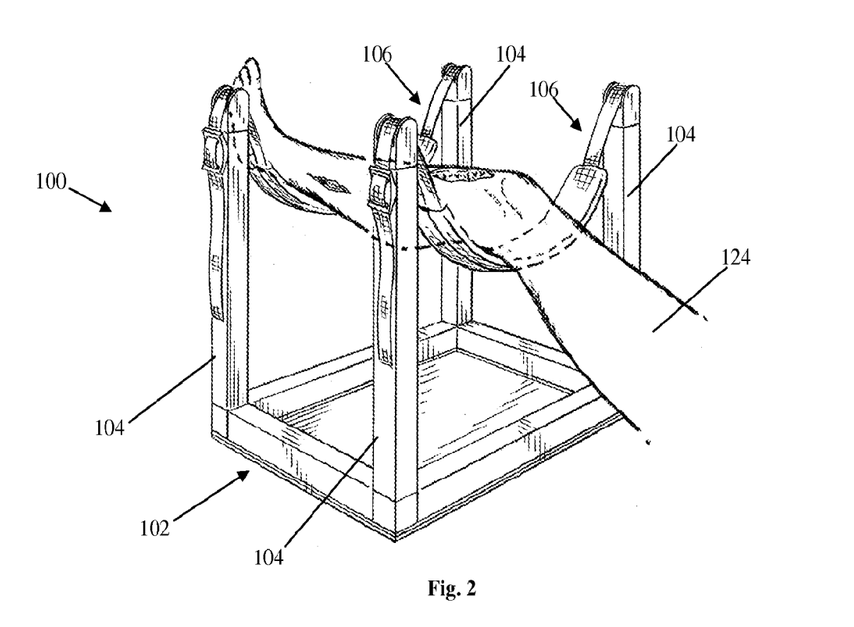
FIG. 2 is a perspective view illustrating the first exemplary embodiment of the present invention shown in FIG. 1 with a patient's extremity positioned thereon.

For the sake of convenience and clarity, terms such as "front," "rear," "top," "bottom," "up," "down," "inwardly," "outwardly," "lateral," and "longitudinal" will be used herein to describe the relative placement and orientation of the various components of the invention, all with respect to the geometry and orientation of the first exemplary embodiment of the device as it appears in FIGS. 1 and 2, with the term "longitudinal" defined as the direction in which the leg shown in FIG. 2 is extending, and the term "lateral" defined as a direction perpendicular thereto. Said terminology will include the words specifically mentioned, derivatives thereof, and words of similar import.

Figures 3, 4, 5:
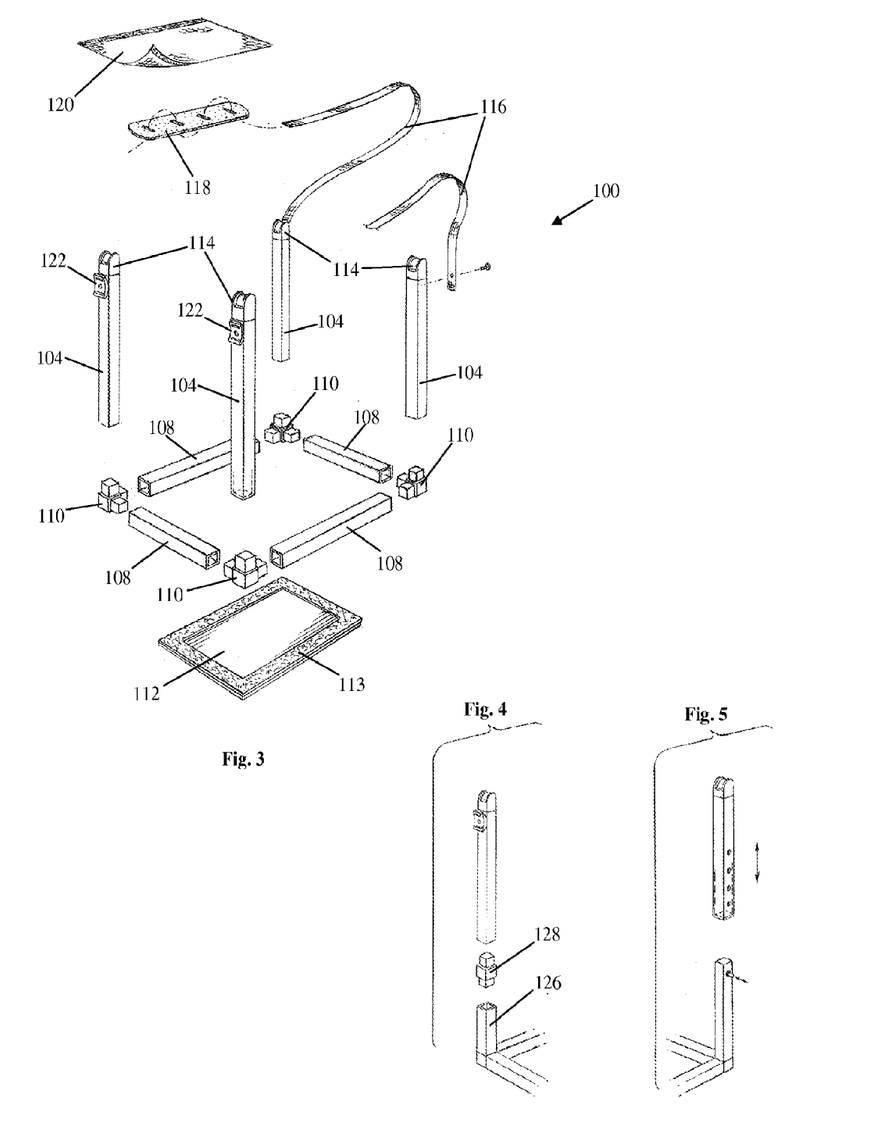
FIG. 3 is an exploded view illustrating the first exemplary embodiment of the present invention shown in FIG. 1.
FIG. 4 is detail view illustrating an extension segment and an adapter bit for extending the dimensions of present invention.
FIG. 5 is detail view illustrating a slidably-lockable, telescoping, alternative configuration the present invention.

Referring to FIGS. 1-3, a first exemplary embodiment of the inventive device, indicated generally at 100, is illustrated. Relative to other embodiments of the invention described herein (i.e., devices 200 and 300 described below), the device 100 is moderately portable, moderately durable, and is moderately costly to produce. It is contemplated that the device 100 would be most suitable for use in extended care facilities, outpatient wound centers, and similar environments where the device would be subjected to moderately frequent use and moderately frequent transportation involving medium distances (e.g., between rooms within a facility).

The device 100 includes a base, indicated generally at 102, upstanding support members 104, and extremity securing mechanisms, indicated generally at 106. The base 102 is a generally rectangular frame formed of four beams 108 that are removably connected to one another by four corner segments 110. The beams 108 are formed of aluminum rectangular tubing, although it is contemplated that the beams 108 can be formed of any other suitably rigid and preferably lightweight material, including, but not limited to tubular or solid segments of steel, plastic, wood, titanium, carbon fiber, or various other fiber-reinforced composites.

Referring to FIG. 3, each of the corner segments 110 is a unitary body having three legs that intersect and terminate at a common corner. Two of the legs are separated from one another by an angle of 90 degrees along a horizontal plane, and the third leg is separated from the other two legs by an angle of 90 degrees along a vertical plane, similar to the configuration of conventional XYZ axes. The corner segments 110 are formed of rigid plastic, although it is contemplated that they can alternatively be formed of any other suitably rigid and preferably lightweight material, including, but not limited to aluminum, wood, graphite, carbon fiber, or other fiber-reinforced composites.

Each leg of the corner segments 110 has a square cross-section with outer dimensions that are substantially equal to, or slightly smaller than, the inner dimensions of the beams 108 of the base 102. The two horizontally-oriented legs of each corner segment therefore fit axially within an end of a beam of the base 102 and are securely held therein by moderately tight frictional engagement. Such frictional engagement allows a user, through the application of moderate manual force, to axially pull the corner segments 110 and beams 108 of the base 102 apart from one another. The device 100 can thereby be conveniently disassembled and stored when it is being transported or is otherwise not in use. It is contemplated, however, that the corner segments 110 and beams 108 can be additionally or alternatively mounted together by various other removable or non-removable means, such as by conventional adhesives or fasteners, or by snap-fitting. It is further contemplated that the corner segments 110 can be omitted and that the beams 108 of the base 102 can be directly mounted to one another, such as by welding or by any of the connective means already discussed. It is further contemplated that the base 102 can alternatively be formed from a single, contiguous piece of material, either in the shape of a frame or as a solid sheet or block, and that the described segments and fastening means can be entirely omitted. Although the upstanding support members 104 are shown parallel to one another, it is contemplated that they can extend outwardly from one another to form a V-shaped longitudinal passage.

Still referring to FIG. 3, a generally planar, rectangular bracing panel 112 is mounted to the bottom of the base 102 for providing the base 102 with added rigidity and for preventing a patient's bodily fluids (e.g., blood from an open wound) and/or treatment substances (e.g., topical medications) from dripping through the base 102 and onto underlying surfaces such as bed sheets. The bracing panel 112 has a length and a width that are substantially identical to the length and width of the base 102, and the edges of the bracing panel 112 are aligned with the outer edges of the base 102, although it is contemplated that the outer dimensions of the bracing panel 112 can exceed those of the base 102. The bracing panel 112 is formed of plastic and is fastened to the underside of the beams 108 of the base by double-sided foam tape 113, although it is contemplated that any other suitably rigid material can be used to form the bracing panel 112 and that any other permanent or removable fastening means, such as conventional fasteners, adhesives, or Velcro can alternatively be used to mount the bracing panel 112 to the base 102. It is further contemplated that the bracing panel 112 can be entirely omitted from the device 100.

The upstanding support members 104 are preferably substantially identical in structure to the beams 108 of the base 102 and are axially attached to the upwardly directed legs of the corner segments 110 of the base 102 in a similar manner (i.e., via axial engagement and friction fit as described above). Like the beams 108 of the base, the upstanding support members 104 can be manually pulled apart from the corner segments 110 to facilitate convenient disassembly of the device 100 for storage and transportation.

Each of the upstanding support members 104 terminates at its upper end in a strap support bit 114. Like the corner segments 110 of the base 102 described above, each strap support bit is formed of plastic and has a downwardly-extending leg with a square cross section (not within view) that fits axially into, and is frictionally held within, the upper end of its corresponding upstanding support member 104. Each strap support bit 114 includes an upwardly-facing central track having a rounded top surface, and guide walls extending upwardly from two opposing edges of the central track to form a channel. The central track is preferably about 1 inch wide, although it is contemplated that the central track can be wider or narrower depending on the width of flexible strap used (described in greater detail below). Each strap support bit 114 is oriented with its guide walls laterally aligned with, and substantially parallel to, the guide walls of the strap support bit 114 on the laterally-opposite side of the device 100.

Referring to FIGS. 1 and 3, each of the extremity securing mechanisms 106 includes a resilient flexible strap 116, a support pad 118, and a cover sleeve 120 (only one support pad and one cover sleeve are shown in FIG. 3 for clarity). The flexible straps 116 are formed of conventional 1 inch wide nylon strap, although it is contemplated that the flexible straps 116 can be formed of any other flexible material, including, but not limited to polyester, rayon, cotton, plastic, silicone, rubber, and various other material blends and composites. It is further contemplated that structures such as bungee cords, conventional ropes and cables, and elastic bands can be substituted for the nylon straps. Still further, it is contemplated that generally inflexible materials, such as aluminum, wood, and hardened plastics can be substituted for the nylon straps, although such materials are generally not preferred for providing optimal comfort as will become apparent herein.

Each flexible strap 116 is affixed at or near one end to a laterally outwardly-facing surface of one upstanding support member 104, preferably by a conventional rivet. From their respective points of attachment, the flexible straps 116 extend upwardly, over the central tracks of their adjacent strap support bits 114, laterally across the width of the device 100 to the opposing upstanding support members 104. The straps 116 extend over the central tracks of the opposing strap support bits 114, and then downwardly into operative engagement with the conventional cam buckles 122 that are rigidly mounted to the laterally outwardly-facing surfaces of the opposing upstanding support members 114. A central expanse of each flexible strap 116 is thereby suspended between each laterally-opposing pair of strap support bits 114, and the guide walls of the strap support bits 114 limit the ability of the flexible straps 116 from moving longitudinally off of their respective central tracks.

The central expanses of the flexible straps 116 preferably have a length that is greater than the distance between the laterally-opposing upstanding support members 104 for allowing the flexible straps 116 to hang between the strap support bits 114 in a slackened, U-shaped configuration as shown in FIGS. 1 and 2. By adjusting the flexible straps 116 relative to their respective cam buckles 122 in a conventional manner, the length of strap 116 between the upstanding support members can be decreased or increased in order to raise or lower the central portions of the flexible straps 116, respectively.

It is contemplated that any or all of the strap support bits 114 and cam buckles 122 can be omitted from the device 100, and that the flexible straps 116 can be secured to the upstanding support members 104 in various different ways. For example, it is contemplated that forked caps can be substituted for the strap support bits 114, and that the flexible straps 116 can terminate at both ends in J-hooks for engaging the forked caps. It is further contemplated that the flexible straps 116 can be riveted at both ends directly to the upstanding support members 104. Other attachment mechanisms well known for attaching and adjusting the lengths of straps and belts can be substituted for the structures shown and described.

The support pads 118 are formed of 2 inch wide segments of flexible plastic. Each support pad 118 has a series of four longitudinally-oriented, parallel slits formed therein. The flexible straps 116 are laced through the slits of the support pads 118 with the support pads 118 being laterally centered along the central portions of the flexible straps 116. The support pads 118 thereby provide a larger surface area upon which a patient's extremity can be supported (as described below) than would be provided by the narrower flexible straps 116 alone, and thus provide a patient's extremity with better weight distribution and a greater degree of stability and comfort. It is contemplated that the support pads 118 can alternatively be formed of any other suitably resilient and flexible material, such as rubber, nylon, polyester, and various composites. Still further, it is contemplated that the support pads 118 can be omitted from the device 100.

The cover sleeves 120 are elongated cuffs of nylon fabric (shown unfurled in FIG. 3) that fit over and surround the support pads 118 and flexible straps 116 in the manner of conventional seat belt pads. When the flexible straps 116 are completely withdrawn from their respective cam buckles 122, the cover sleeves 120 can be slipped onto, or off of, the support pads 118 and flexible straps 116, thereby providing the device 100 with patient-interface surfaces that can be conveniently removed and sanitized or replaced between uses. Although nylon fabric is preferred for its light weight and impermeability to most liquids, it is contemplated that the cover sleeves 120 can additionally or alternatively be formed of various other types of fabrics or materials, such as rayon, polyester, cotton, linen, plastic, GORE-TEX, non-wovens, and rubber. It is further contemplated that the cover sleeves 120 can be secured about the support pads 118 using Velcro or other removable fasteners for allowing the cover sleeves 120 to be conveniently removed from the support pads 118 without first having to withdraw the flexible straps 116 from the cam buckles 122. Still further, it is contemplated that the cover sleeves 120 can be entirely omitted from the device 100.

During use of the device, a patient's extremity, such as the leg 124 shown in FIG. 2, can be positioned on the extremity securing mechanisms 106 of the device 100 for examination and treatment. For example, still referring to FIG. 2, in order to examine and treat the calf area of the leg 124, it is contemplated that, after adjusting the central portions of the flexible straps 116 to a desired height (as described above), the patient's ankle can be brought to rest on the rear-most extremity securing mechanism 106 and the patient's upper calf can be brought to rest on the forward-most extremity securing mechanism 106. Alternatively, if a patient's extremity is too delicate or too heavy to be manually lifted onto the device, the central portions of the flexible straps 116 can instead first be lowered to a height adjacent the device's base 102. The patient's extremity can then be moved onto the extremity securing mechanisms 106, and the flexible straps 116 can subsequently be adjusted relative to their respective cam buckles 122 to reduce the amount of slack in the central portions of the flexible straps 116 in order to raise the extremity to a desired height.

In some instances, it may be desirable to vary the dimensions of the device 100 in order to effectively accommodate patients having larger or smaller extremities. It is therefore contemplated that the device can be provided with additional beams and upstanding support members of different incremental lengths for configuring the device 100 with different heights, widths, and lengths. Alternatively, Referring to FIG. 4, the device can be provided with tubular extension segments, such as extension segment 126, and male-to-male adapter bits, such as adapter bit 128 having two oppositely directed legs that are substantially identical to the legs of the corner segments 110 and strap support bits 114 described above. The adapter bits thereby allow the extension segments to be axially connected to any of the beams 108 or upstanding support members 104 in the manner illustrated in FIG. 4. It is contemplated that female-to-female adapter bits can similarly be used to connect the extensions segments to the beams or upstanding support members. The extension bits can be provided in a variety of different lengths for increasing the length, width, and height of the device and extremity securing mechanisms 106 as necessary. Referring to FIG. 5, it is further contemplated that the device 100 can alternatively or additionally be provided with telescopic beams or upstanding support members that feature spring-loaded locking mechanisms for allowing the length, width, and height of the device 100 to be slidably adjusted and secured.

Figure 6:
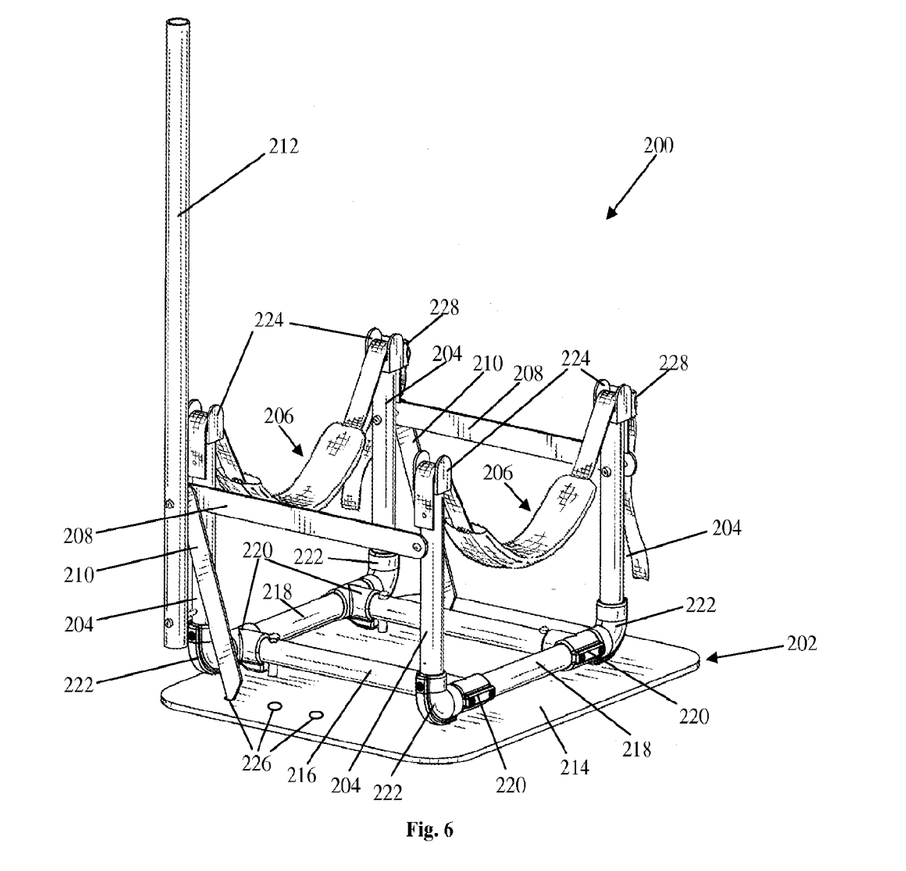
FIG. 6 is a perspective view illustrating a second exemplary embodiment of the present invention in an upright position.

Referring now to FIG. 6, a second exemplary embodiment of the inventive device, indicated generally at 200, is illustrated. Relative to the other embodiments of the invention described herein (i.e., device 100 described above and device 300 described below), the device 200 is minimally portable (i.e., larger and heavier), more durable, and is generally more costly to produce. It is contemplated that the device 200 is best suited for use in environments such as surgical suites where the device 200 would be subjected to frequent extended use and little or no transportation involving long distances (i.e., the device would generally be stored and used in the same room or series of rooms), and where the structural integrity of the device is of great importance (e.g., during surgery).

Like the device 100 described above, the device 200 includes a base, indicated generally at 202, upstanding support members 204, and extremity securing mechanisms, indicated generally at 206. The device 200 further includes cross members 208, support stands 210, and a pivot bar 212. Unless otherwise noted, the components of the device 200 are formed of stainless steel, although it is contemplated that any of the components can be formed of any other suitably rigid material, including, but not limited to aluminum, titanium, wood, various plastics, or various composites.

The base 202 of the device 200 includes a base plate 214, two fixed arms 216, and two pivot arms 218. The base plate 214 is formed of a planar sheet of rigid plastic, although it is contemplated that the base plate 214 can be formed of any other suitably rigid and preferably lightweight material, such as those discussed above. The fixed arms 216 of the base 202 are each formed of a tubular segment that is rigidly mounted to the base plate 214 by a pair of bolts. The fixed arms 216 are spaced apart from one another in a parallel configuration, and each fixed arm 216 terminates at each of its longitudinal ends in a tubular, T-shaped fitting 220 that is rigidly but removably mounted thereto. Each T-shaped fitting 220 is oriented with the top segment of its "T" axially aligned with the top segment of the "T" of a laterally adjacent T-shaped fitting 220 to form a pair of aligned bearing bores.

The pivot arms 218 are each formed of a tubular segment that extends laterally through the axially aligned bores of a pair of laterally adjacent T-shaped fittings 220. The inner diameters of the portions of the T-shaped fittings 220 through which the pivot arms 218 extend are slightly greater than the outer diameters of the pivot arms 218. The pivot arms 218 are thereby rotatably held within the T-shaped fittings 220 in a snug radial relationship, but are able to rotate freely about their respective axes. Each pivot arm 218 terminates at each of its lateral ends in an elbow fitting 222 that is rigidly but removably mounted thereto.

Still referring to FIG. 6, the upstanding support members 204 are each formed of a tubular segment that is rigidly but removably mounted to an elbow fitting 222. The upstanding support members 204 extend upwardly from the elbow fittings 222 and terminate at their top ends in strap support bits 224 that are substantially identical to the strap support bits 114 of the device 100 described above, except that the strap support bits 224 of the device 200 each have a leg (not within view) with a circular cross section for axially engaging and mounting within the cylindrical upstanding support members 204.

Figure 7:
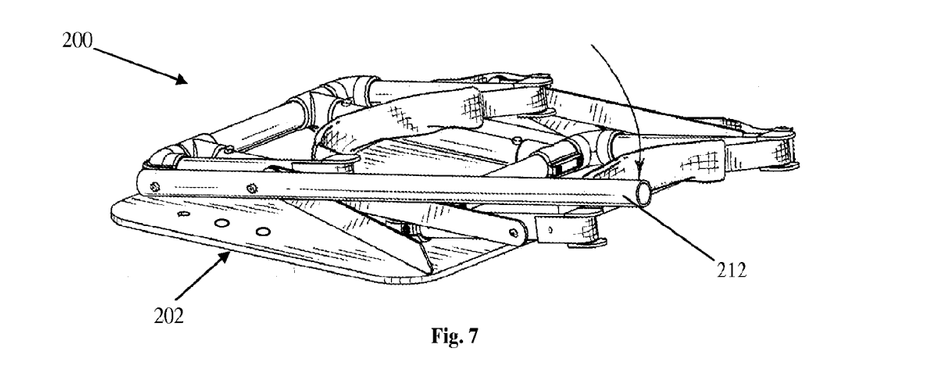
FIG. 7 is a perspective view illustrating the second exemplary embodiment of the present invention shown in FIG. 6 in a collapsed position.

The cross members 208 are elongated plates that connect each upstanding support member 204 of the device 200 to a longitudinally-adjacent upstanding support member 204 of the device 200. Each cross member 208 is pivotably fastened at each of its ends to an upstanding support member 204 by a single rivet. All of the upstanding support members 204 are thereby connected to one another (i.e., either by cross members 208 or by pivot arms 218), and the device 200 is thus configured in the manner of a 4-point linkage that is able to rotate about the axes of the pivot arms 218 between an upright position (as shown in FIG. 6) and a collapsed position (as shown in FIG. 7).

The support stands 210 are elongated plates that are pivotably connected to the rearmost upstanding support members 204. Each support stand 210 is mounted to its respective upstanding support member 204 by a single, laterally-oriented rivet, and is thus able to articulate through a vertical plane. Each support stand 210 terminates in a pointed lower end for engaging any of a series of stand apertures 226 formed in the base plate 214. Each of support stands 210 can thereby be pivotably extended away from the upstanding support members 204 and moved into engagement with one of the stand apertures 226 for propping the device 200 in any of a number of positions between the collapsed position and the upright position, thus functioning in the manner of conventional bicycle kickstands for preventing the device 200 from collapsing toward a patient during use. The support stands 210 can be subsequently removed from the stand apertures 226 and pivotably retracted to an orientation substantially parallel with their respective upstanding support members 204 for allowing the device 200 to be collapsed.

The lift handle 212 is an elongated tubular segment that is bolted to one of the rearmost upstanding support members 204 in a parallel orientation thereto. The lift handle 212 extends to a height well above the tops of the upstanding support members 204 and provides users of the device 200 with a lever for conveniently pivoting the device 200 between its upstanding and collapsed positions. Although the particular lift handle 212 has been shown to work well within the context of the device 200, it is contemplated that various other mechanical or electromechanical means can additionally or alternatively be incorporated for conveniently raising and collapsing the device 200. For example, a conventional winch and cable assembly can be mounted to the base plate 214 and adapted to raise and collapse the device 200. Alternatively, it is contemplated that conventional pneumatic or hydraulic rams can be used to raise and collapse the device 200. Still further it is contemplated that all such mechanical and electromechanical means, including the lift handle 212, can be entirely omitted from the device 200.

Still referring to FIG. 6, the extremity securing mechanisms 206 and cooperating cam buckles 228 of the device 200 are substantially identical to the extremity securing mechanisms 106 and cam buckles 122 of the device 100 described above. As with the device 100, a patient's extremity can be lifted onto and extended longitudinally across the extremity securing mechanisms 206 of the upstanding device 200 for examination and treatment. Alternatively, a patient's extremity can be lifted onto and extended longitudinally across the extremity securing mechanisms 206 of the device 200 while the device 200 is in its collapsed position, and a caregiver can subsequently pivot the device 200 to its upstanding position using the lift handle 212. This method of lifting a patient's extremity is especially useful for lifting heavy or delicate extremities, where manually lifting the extremity may be too difficult or may cause injury to the caregiver or the patient.

It is contemplated that the device 200 can be provided with any of the previously described adjustment means, such as substitute components of various different lengths, additional extension segments with adapter bits, or telescoping components for varying the dimensions of the device 200 as desired.

Figure 8:
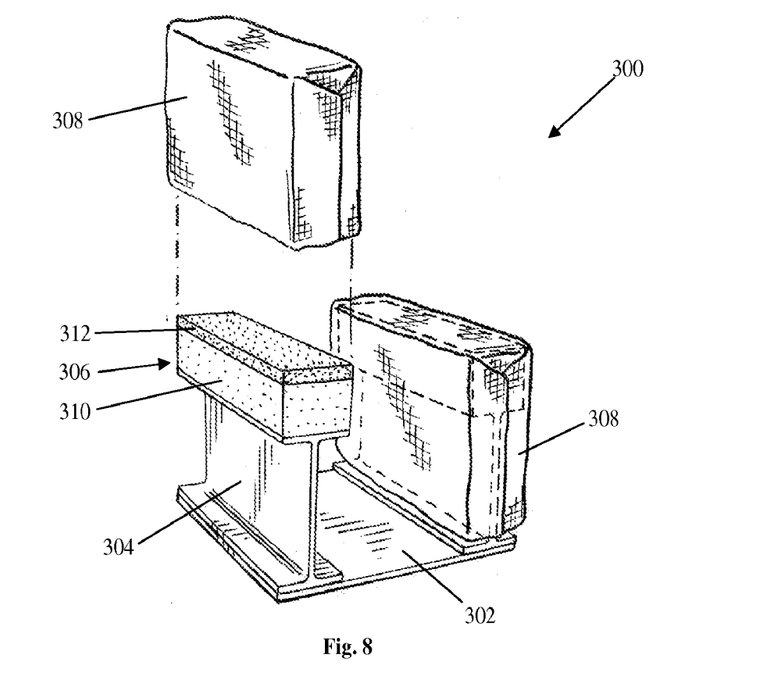
FIG. 8 is a perspective view illustrating a third exemplary embodiment of the present invention.

Referring now to FIG. 8, a third exemplary embodiment of the inventive device, indicated generally at 300, is illustrated. Relative to the other embodiments of the invention described herein (i.e., devices 100 and 200 described above), the device 300 is highly portable (i.e., smaller and lighter), less durable, and is generally less costly to produce. It is contemplated that the device 300 is best suited for use in environments such as home care, where the device would be subjected to minimal use (i.e., single patient) and frequent transportation involving medium to long distances (i.e., between hospital and home, between rooms within a home, and between home and other locations where a patient may choose to travel), and where the structural integrity of the device 300 is of less concern (i.e., during less sensitive procedures such as routine examination and wound dressing which commonly take place in home care environments).

The device 300 includes a base plate 302, upright support members 304, extremity securing mechanisms, indicated generally at 306, and removable cover sleeves 308. The base plate 302 and upstanding support members are formed of high strength plastic, although it is contemplated that the base plate 302 can be formed of any other suitably rigid, durable, and preferably lightweight material, such as aluminum, titanium, stainless steel, graphite, carbon fiber, wood, other plastics, and various composites. The upright support members 304 are I-beams that are mounted to the planar base plate 302 in a longitudinally-spaced, laterally-extending, parallel configuration. The bottom surfaces of the upstanding support members 304 are rigidly affixed to the base plate 304 with epoxy, although it is contemplated that the support members can be affixed to the base plate 302 using any other permanent or removable means, such as with various conventional fasteners or adhesives.

The extremity securing mechanisms 306 include rectangular blocks of foam rubber 310 and silicone pads 312. The foam rubber blocks 310 are affixed to the top surfaces of the upstanding support members 304 with epoxy, although it is contemplated that the foam rubber blocks 310 can be mounted to the upstanding support members 304 using any other conventional removable or permanent means, such as those described above. The silicone pads 312 are positioned on the top surfaces of the foam rubber blocks 310 with no means of attachment holding them in place other than frictional engagement between the bottom surfaces of the silicone pads 312 and the top surfaces of the rubber blocks 310. It is contemplated that the silicone pads 312 can be permanently or removably affixed to the rubber blocks 310 by any conventional means, such as those described above.

The cover sleeves 308 are formed of nylon fabric and each has an open bottom, a closed top, and a length and a width that are substantially equal to the length and the width of the extremity securing mechanisms 306. The cover sleeves can thereby be easily pulled onto or off of the extremity securing mechanisms 306 for providing the device 300 with patient-interface surfaces that can be conveniently removed and sanitized or replaced between uses. As with the cover sleeves 120 of the device 100 described above, it is contemplated that the cover sleeves 308 can be formed of a variety of different materials or can be entirely omitted from the device 300.

As with the devices 100 and 200 described above, a patient's extremity can be lifted onto and extended longitudinally or laterally across the extremity securing mechanisms 306 of the device 300 for examination and treatment. The silicone pads 312 provide soft, pliable surfaces for comfortably cradling a patient's extremity, while the foam rubber blocks 310 provide a resilient, shock absorbent support for the extremity. It is contemplated that a variety of alternative materials and material combinations can be substituted for either or both of the foam rubber blocks 310 and the silicone pad 312, such as various different types of padding, mats, or cushions. It is further contemplated that the silicone pads 312, as well as any alternatives thereof, can be entirely omitted from the device 300.

Figure 9:
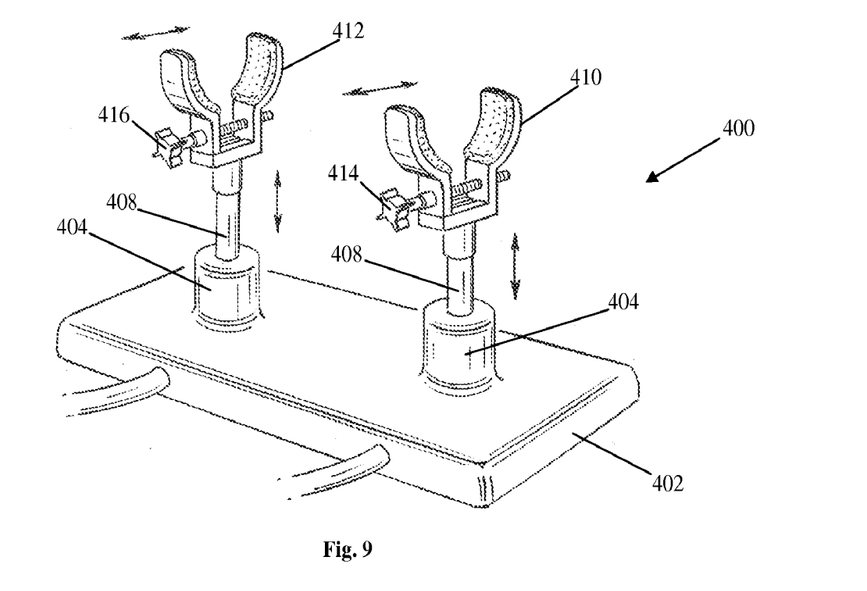
FIG. 9 is a perspective view illustrating a fourth exemplary embodiment of the present invention.

FIG. 9 illustrates a fourth alternative embodiment of the inventive device, indicated generally at 400, which includes an elongated rectangular base 402, upstanding support members 404, and extremity securing mechanisms, indicated generally at 406. The upstanding support members 406 are substantially tubular structures that extend upwardly from the base 402 in a longitudinally-spaced relationship.

The extremity securing mechanisms 406 include lift pistons 408 that axially protrude from the upstanding support members 404 and terminate in first and second yokes 410 and 412 that are rigidly secured to the tops of the lift pistons 408. The yokes 410 and 412 cradle and support a patient's longitudinally-extended extremity to facilitate assessment and treatment. For example, a patient's wrist may rest on the rearmost yoke 412 and a patient's upper arm may rest on the yoke 410. Each yoke 410 and 412 is separated into two laterally-opposing arcuate segments that are adjustably attached to one another, such as by a threaded rod, for allowing the width of each yoke 410 and 412 to be adjusted by rotating the adjustment knobs 414 and 416. The device 400 can thereby be easily adjusted to accommodate extremities of different sizes. Preferably, at least the inwardly facing portions of each of the yokes 410 and 412 is padded for providing patients with increased comfort.

The lift pistons 408 are hydraulically operated, such as with a foot pedal (not shown), for raising and lowering the yokes 410 and 412 and positioning a patient's extremity at a desired height. Alternatively, it is contemplated that the lift pistons 408 can be pneumatically operated, or that the lift pistons 408 can be replaced by telescoping shafts that are operatively driven by an electric motor. It is further contemplated the lift pistons 408 can be replaced by manually-adjustable, telescoping shafts that can be slidably locked at various incremental heights through the incorporation of frictional detents, locking pins, or spring-loaded locking mechanisms formed or mounted on such shafts.

Figure 10:
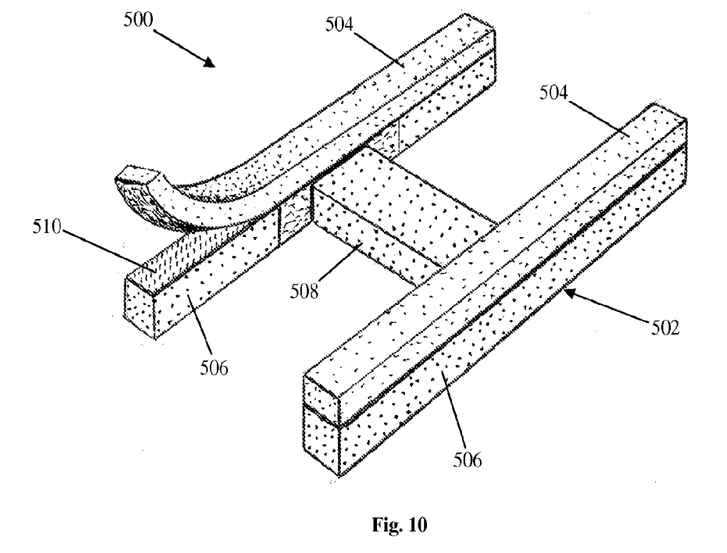
FIG. 10 is a perspective view illustrating a fifth exemplary embodiment of the present invention.

FIG. 10 illustrates a fifth alternative embodiment of the inventive device, indicated generally at 500, which includes a base, indicated generally at 502, and extremity securing mechanisms 504. The base 502 is formed of foam block and has an H-shaped configuration with two legs 506 connected by a cross member 508. The extremity securing mechanisms 504 are also formed of foam block and are removably secured to the legs 506 of the base with Velcro strips 510 (only one of the Velcro strips is visible in FIG. 10). The extremity securing mechanisms 504 can thereby be easily detached from the base 502 to be sanitized or replaced.

It is contemplated that the components of the device 500 can be formed of foams having different firmnesses. For example, the base 502 can be formed of relatively hard foam, while the extremity securing mechanisms 504 can be formed of softer, less dense foam for comfort. As with the embodiments of the inventive device described above, a patient's extremity can be lifted onto and extended across the extremity securing mechanisms 504 of the device 500 for examination and treatment. It is contemplated that the device 500 may be modified with additional foam support blocks interposed between the base 502 and one or both of the extremity securing mechanisms 504 to elevate a patient's extremity as desired.

Figure 11:
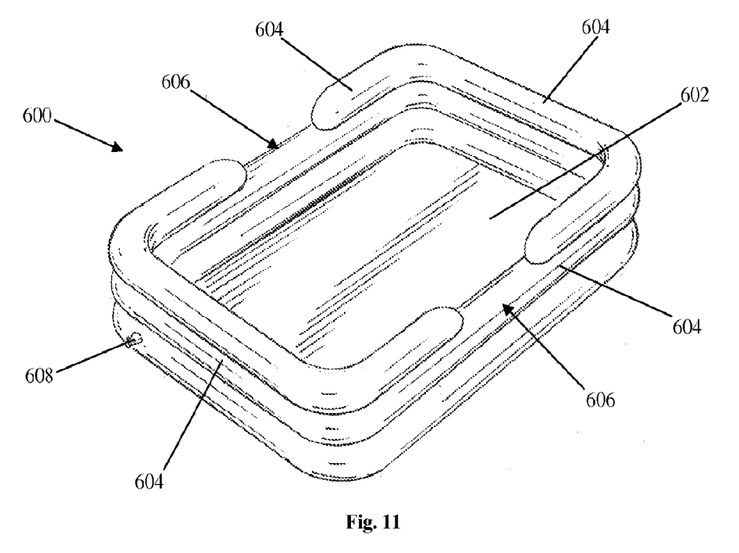
FIG. 11 is a perspective view illustrating a sixth exemplary embodiment of the present invention.

FIG. 11 illustrates a sixth alternative embodiment of the inventive device, indicated generally at 600, which includes a bladder having a rectangular base 602 and upstanding support members 604 that define a contiguous, inflatable chamber. The upstanding support members 604 are walls that extend upwardly from each edge of the base 602. Each of the longitudinally-opposing upstanding support members 604 has a central notch 606 formed in its top edge, and these notches 606 are longitudinally aligned to provide spaces within which a patient's longitudinally-extended extremity can be seated, and thus provided with both vertical and lateral support by the edges of the upstanding support members 604 that define the notches 606. Alternatively, it is contemplated that the notches 606 can be omitted and that a patient's extremity can instead be supported by the top edges of the longitudinally-opposing upstanding support members 604. It is further contemplated that the laterally-opposing upstanding support members 604 (i.e., the upstanding support members which a patient's extremity does not extend across) can be omitted.

The device 600 is provided with a conventional spout 608, such as those incorporated in inflatable mattresses, for inflating and deflating the device 600. An advantage of the device 600 is that the deflated, generally planar bladder can be positioned beneath a patient's extremity and subsequently inflated to elevate the extremity to a desired height. Although is preferred that the bladder be inflated with air, it is contemplated that the device 600 can be formed as a watertight structure and can alternatively be filled with water or other liquids, including cold, warm or hot water (e.g., water at 35° F., 85° F. and 110° F., respectively)

Figure 12:
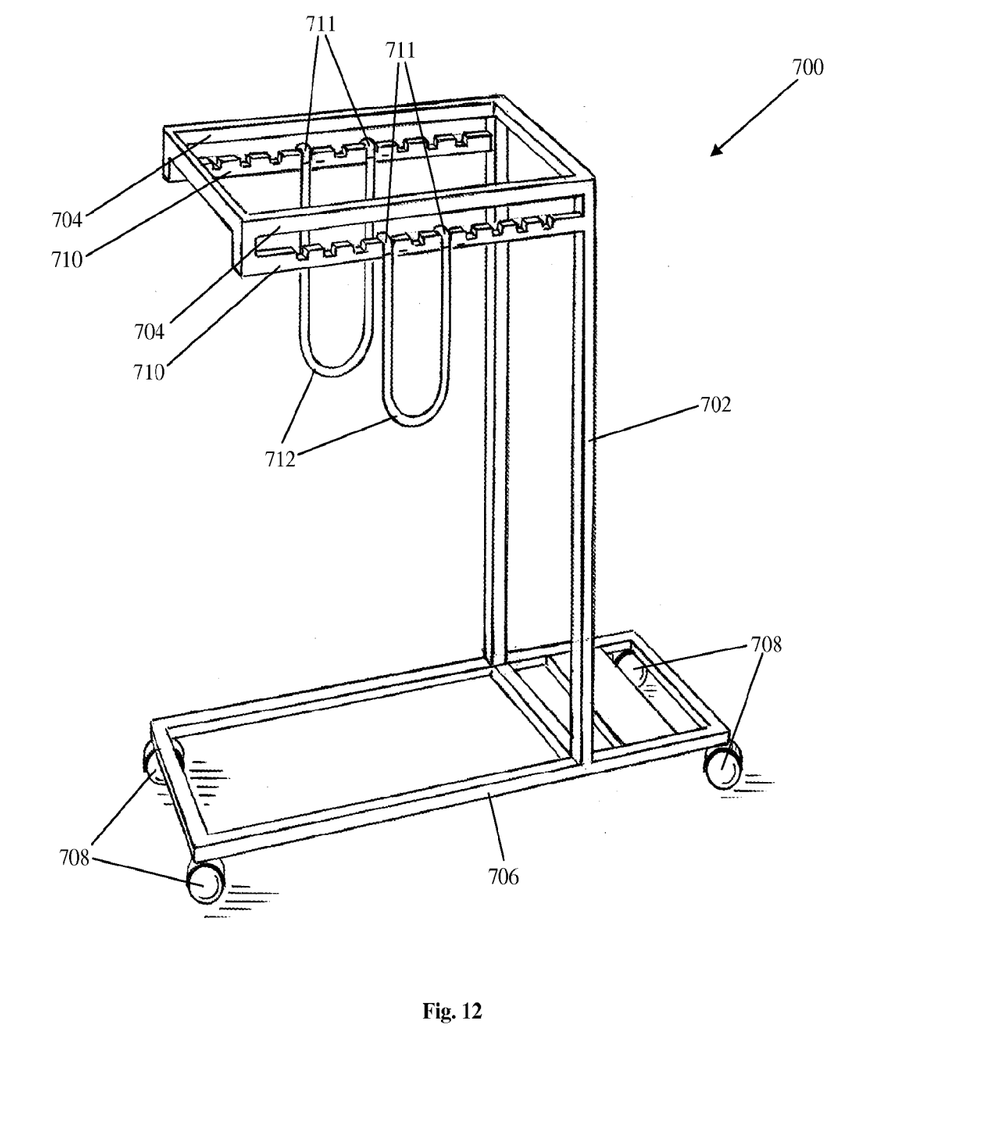
FIG. 12 is a perspective view illustrating a seventh exemplary embodiment of the present invention.

FIG. 12 illustrates a seventh exemplary embodiment of the inventive device, indicated generally at 700, which includes a rectangular vertical frame, indicated generally at 702, having two parallel, longitudinally-spaced support arms 704 extending perpendicularly therefrom. The frame 702 is mounted at its lower end to an elongated rectangular base 706 having wheels 708 for providing the device 700 with convenient portability. The base 706 is configured to fit below a conventional hospital bed with the longitudinally-spaced support arms 704 extending laterally over the bed. One of the support arms 704 is thereby positioned nearer the head of the bed and the other support arm 704 is positioned nearer the foot of the bed.

Suspension bars 710 having notched upper surfaces are mounted below the support arms 704 in a parallel orientation thereto. Flexible slings 712 are hung from each of the suspension bars 710 by hooks 711 that seat within the notches of the suspension bars 710, as shown in FIG. 12. Each sling 712 laterally extends below its respective suspension bar 710 in a slackened, U-shaped configuration, and is longitudinally aligned with the other sling 712. The notches in the suspension bars 710 prevent the hooks 711 from moving laterally along the suspension bars 710 when a limb is suspended therein, and thus allow the lateral position of the slings 712 along the suspension bars to be set and maintained as desired. It is contemplated, however, that the notches can be omitted and that the slings 712 can be removably or permanently mounted to the suspension bars 710 in any conventional manner.

To use the device 700, the extremity of a patient lying in a bed positioned beneath the support arms 704 can be extended through, and brought to rest on, the longitudinally-aligned slings 712. For example, the upper calf of a patient's leg can be brought to rest on the sling 712 nearest the head of the bed, and the patient's ankle can be brought to rest on the sling 712 nearest the foot of the bed. It is contemplated that the length of the slings 712 may be varied to accommodate the particular size of a patient's extremity and the height at which the extremity is to be suspended (i.e., shorter slings for higher suspension). It is further contemplated that two slings can be hung from each of the suspension bars 710 for allowing the device 700 to simultaneously accommodate two of a patient's extremities, such as both of a patient's legs. Still further, pads can be mounted to the lower end of the slings to increase comfort.

Figure 13:
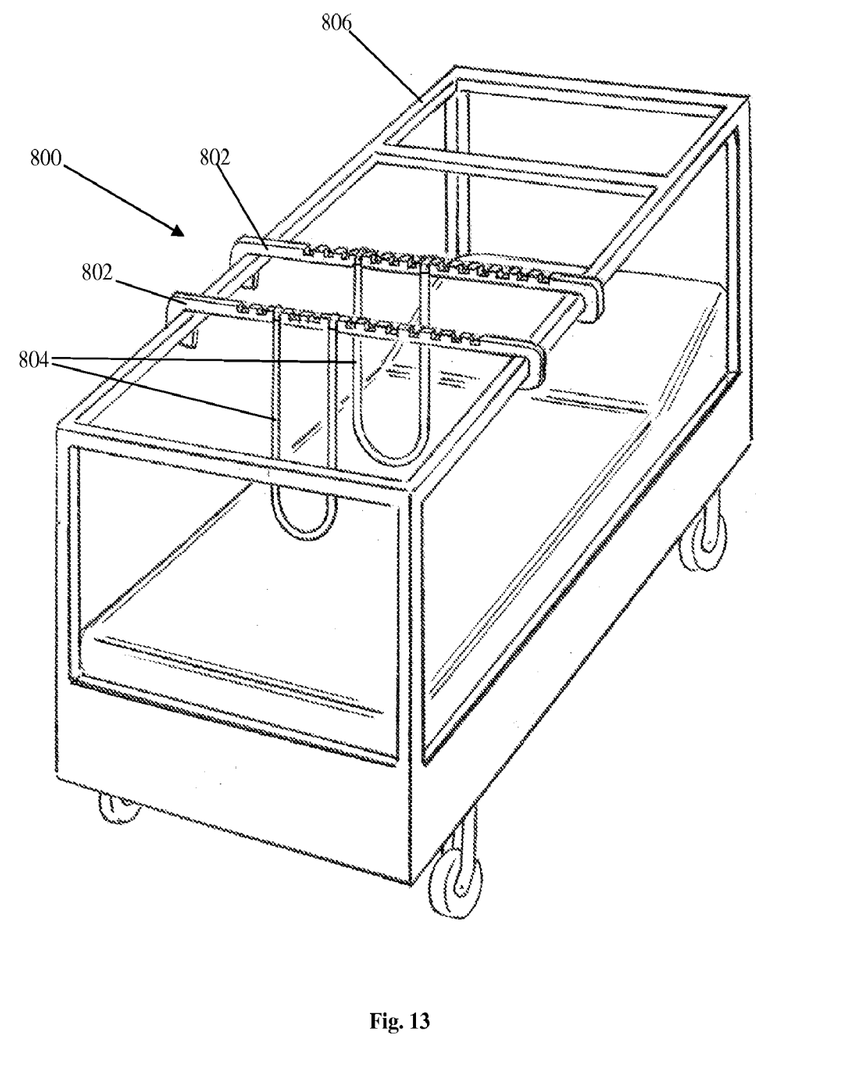
FIG. 13 is a perspective view illustrating a third exemplary embodiment of the present invention mounted to a canopy-style hospital bed.

FIG. 13 illustrates an eighth exemplary embodiment of the inventive device, indicated generally at 800, that includes suspension bars 802 and slings 804 that are substantially identical to those of the device 700 described above. The suspension bars 802 are removably mounted to the laterally-opposing upper crossbars of a conventional canopy bed frame, such as the bed frame 806, in a longitudinally-spaced relationship. The device 800 is otherwise used in a manner identical to the device 700 (i.e., mounting the slings 804 on the suspension bars 802 in a longitudinally-aligned relationship and extending a patient's extremity through the slings 804).

This detailed description in connection with the drawings is intended principally as a description of the presently preferred embodiments of the invention, and is not intended to represent the only form in which the present invention may be constructed or utilized. The description sets forth the designs, functions, means, and methods of implementing the invention in connection with the illustrated embodiments. It is to be understood, however, that the same or equivalent functions and features may be accomplished by different embodiments that are also intended to be encompassed within the spirit and scope of the invention and that various modifications may be adopted without departing from the invention or scope of the following claims.

The invention claimed is:

1. An extremity assessment and management device for supporting at least one of a patient's extremities in an elevated position to facilitate access to said at least one extremity, the device comprising:
   a. a planar base comprising fixed pivot points;
   b. at least first and second pairs of upstanding support members pivotably connected to the base through said fixed pivot points on the base and secured to one another in a parallel configuration allowing said at least first and second pairs of upstanding support members to be simultaneously and uniformly pivoted between a collapsed position, wherein each of the upstanding support members is folded against the base, and an upright position, wherein each of the upstanding support members is transverse to the base; and
   c. at least a first and a second extremity securing mechanism, each mounted to a different one of said upstanding support members for engaging and supporting said at least one extremity; and
   wherein each of said extremity securing mechanisms extends across one of the first and second pairs of upstanding support members.

2. The extremity assessment and management device in accordance with claim 1, wherein each of said extremity securing mechanisms comprises a flexible strap.

3. The extremity assessment and management device in accordance with claim 2, wherein each of said extremity securing mechanisms further comprises a support pad mounted to a central portion of the flexible strap.

4. The extremity assessment and management device in accordance with claim 3, wherein each of said extremity securing mechanisms further comprises a removable cover sleeve that fits over at least a portion of the support pad.

5. The extremity assessment and management device in accordance with claim 1, further comprising an elongated lift bar removably mounted to at least one of the upstanding support members and extending beyond said support members for pivoting the upstanding support members between the collapsed position and the upright position relative to the base.

6. The extremity assessment and management device in accordance with claim 5, further comprising at least one elongated support stand having a proximal end that is pivotably mounted to one of said upstanding support members and a distal end that removably engages the base for preventing the upstanding support members from folding to the collapsed position.

* * * * *